Figure 1:
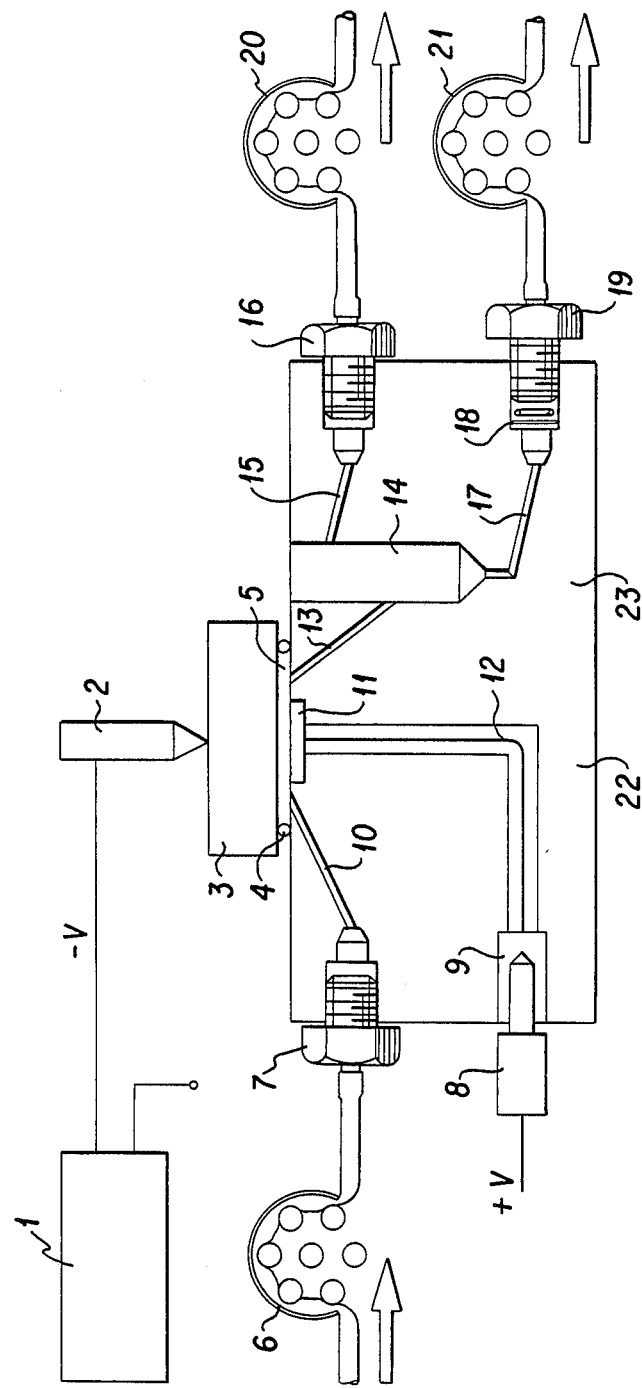

United States Patent [19]

Arruda et al.

[11] Patent Number: 4,737,255

[45] Date of Patent: Apr. 12, 1988

[54] APPARATUS FOR RAPID DISSOLVING OF METAL ALLOY SAMPLE FOR CHEMICAL ANALYSIS

[75] Inventors: Elpidio C. Arruda; Carlos A. Coutinho, both of Castelo, Brazil

[73] Assignee: 501 Usinas Siderugicas de Minas Gerais S/A, Brazil

[21] Appl. No.: 944,986

[22] Filed: Dec. 19, 1986

[51] Int. Cl.[4] .................. C25C 7/00; G01N 27/26
[52] U.S. Cl. .................................. 204/278; 204/400
[58] Field of Search ............... 204/242, 278, 400, 435

[56] References Cited

U.S. PATENT DOCUMENTS

| | | | |
|---|---|---|---|
| 2,319,196 | 5/1943 | Anderson et al. | 204/434 |
| 2,457,234 | 12/1948 | Herbert et al. | 204/434 |
| 2,531,747 | 11/1950 | Stearn | 204/400 |
| 3,492,217 | 1/1970 | Keeler et al. | 204/278 X |
| 4,310,389 | 1/1982 | Harbulak | 204/434 X |

Primary Examiner—Donald R. Valentine
Attorney, Agent, or Firm—Anthony A. O'Brien

[57] ABSTRACT

A dissolving cell for the continuous processing of a sample, having a dissolving chamber enclosed by the sample, a seal and the body of the cell in combination with an anode. The cell includes a cathode and a D.C. power source for effecting the dissolution of the sample through an electrolyte conveyed to the chamber by an inlet terminal in open communication therewith. The dissolving cell includes a degasing shaft positioned between the dissolving chamber and outlet pipe. A first outlet pipe at the top of the degaser vents gases to a drain and a second outlet pipe communicating with the bottom of the degasser conveys electrolyte with sample to additional processing equipment.

2 Claims, 1 Drawing Sheet

APPARATUS FOR RAPID DISSOLVING OF METAL ALLOY SAMPLE FOR CHEMICAL ANALYSIS

This invention relates to an improvement relating to Brazilian patent applications Nos. PI 8008038 and PI 8104165, consisting basically of modifications in the electrolytic dissolving cell, aiming at continuous dissolving of the sample, for direct analysis in equipment such as flow injection analyzer (Flow Injection Analysis—FIA), atomic absorption spectrophotometer, plasma spectrometer, ionic chromatography, among others.

Application No. PI 8008038 aims only at reducing the sample dissolving time, dealing with a cell with two interconnected compartments which contain the electrolyte. The cathode is located in one of the compartments, where the sample is dissolved. In this same compartment, the sample, connected to a power source, constitutes the anode, having one face immersed in the electrolyte. The other compartment has only the function of a circulation and cooling tank of the electrolyte.

No. PI 8104165 also has the object of rapid dissolving of the sample, exhibiting vertical process flow. The dissolving chamber is placed in the upper part of the equipment, the sample being immersed by one face in the electrolyte. Diaphragm electromagnetic pumps placed coaxially in the lower planes promotes the total draining of the electrolytic solution for later sending to the analysis equipment.

Both patent applications cited above relate to apparatus for electrolyte dissolving in cells that operate by batch, in each operation dissolving a determined amount of metal sample in a volume, also predetermined, of an acid solution (electrolyte).

Considering the more modern analytical methods offer the possibility of continuous injection of the electrolytic solution, this improvment aims at a better compatibilizing between dissolving the sample and the analysis process, making the dissolving step also a continuous process. The invention simplifies automation of the entire analytical process, which is essential to monitoring the metallurgical process, which requires speed and high precision of analysis.

The dissolving apparatus proposed as an invention consists basically of a dissolving cell in which the electrolyte flows continuously through it, all the components of the apparatus being shown in FIG. 1, in which are seen:

1—Power source
2—Anode electric connector
3—Sample
4—Seal
5—Dissolving chamber
6—Peristaltic pump (pipe 1)
7—Electrolyte input terminal
8—Cathode electric connector
9—Electric connector
10—Feed pipe
11—Cathode
12—Electric conductor
13—Output pipe
14—Degasification shaft
15—Overflow pipe
16—Drain
17—Electrolyte output pipe
18—Filter
19—Electric output terminal
20—Peristaltic pump (pipe 2)
21—Peristaltic pump (pipe 3)
22—Cell body
23—Dissolving cell The apparatus is made up of a dissolving cell (23), a peristaltic pump with three pipes (6), (20) and (21), and a dc power source (1).

Cell body (22) is made of electrically insulating material, exhibiting a dissolving chamber (5) formed by body (22), cathode (11), seal (4) and sample (3). Cathode (11) is aligned above with the upper face of body (22), sample (3) being placed parallel to this face. Between body (22) and sample (3) is seal (4) which then forms chamber (5) above cathode (11) and above sample (3).

Cell body (22) also exhibits an input terminal (7) and an output terminal (19) of the electrolyte. Input (7) communicates directly with dissolving chamber (5), by pipe (10) and output (19), with degasification shaft (14) by pipe (13). This shaft exhibits an overflow (15) which allows drainage of excess electrolyte by drain (16).

Dc power source (1) feeds the cell by an electric circuit made up of contacts (8) and (9), conductor (12), cathode (11), sample (3) and anode connector (2).

The electrolyte is continuously brought through input terminal (7) to dissolving chamber (5). Electrolysis is continuously performed in this chamber, since the electrolytic solution containing the dissolved sample is sent to degasification shaft (14) where the gases generated in the electrolysis are released into the atmosphere. The solution, free of gases, leaves by terminal (19) equipped with filter (18), feeding the chemical analysis equipment directly and continuously.

Another version of the cell can be made with body (22), cathode (11), conductor (12) and electric connector (9) made from a single piece of electrically conductive material, then cathode (11) would be constituted by the upper face itself of cell body (22).

We claim:

1. A dissolving cell for rapidly dissolving a metal alloy, comprising:
    a power source, a cathode having a contact connected to the power source and a contact connected to a sample;
    a body of electrically insulating, having a dissolving chamber with the boundary thereof defined by the body in combination with an anode, the sample and a seal;
    an input terminal and a plurality of output terminals in open communication with the dissolving chamber;
    a gasification shaft positioned between the dissolving chamber and the output terminals, wherein a first output terminal collects gasses produced in the dissolving chamber for venting, and a second output terminal conveys an electrolyte and dissolved sample to additional analytical equipment.

2. The dissolving cell according to claim 1 wherein the sample is the upper face of the dissolving chamber, the body in combination with the anode is the bottom face, and the seals the side walls.

* * * * *